United States Patent [19]
Maurer et al.

[11] Patent Number: 5,376,206
[45] Date of Patent: Dec. 27, 1994

[54] METHOD OF MAKING AN INCONTINENCE ELECTRODE

[75] Inventors: Donald D. Maurer, Anoka; Alexander Kipnis, Minneapolis, both of Minn.

[73] Assignee: Empi, Inc., St. Paul, Minn.

[21] Appl. No.: 979,642

[22] Filed: Jan. 4, 1993

Related U.S. Application Data

[62] Division of Ser. No. 675,568, Mar. 26, 1991, Pat. No. 5,199,443.

[51] Int. Cl.5 .............................. B32B 31/06
[52] U.S. Cl. ............................ 156/242; 29/883; 29/884; 264/105; 264/262; 264/272.14; 439/496
[58] Field of Search ............ 29/881, 883, 884; 439/495, 496; 264/104, 262, 105, 272.14; 128/642; 607/40, 41, 134, 135, 138; 156/242

[56] References Cited

U.S. PATENT DOCUMENTS

| | | | |
|---|---|---|---|
| 3,800,800 | 4/1974 | Garbe et al. | 128/408 |
| 3,933,147 | 1/1976 | Du Vall et al. | 128/2 S |
| 4,094,309 | 6/1978 | Grzenia | 128/2.06 |
| 4,296,760 | 10/1981 | Carlsson et al. | |
| 4,785,828 | 11/1988 | Maurer | |
| 4,817,611 | 4/1989 | Arzbaecher et al. | 128/642 |
| 4,873,996 | 10/1989 | Maurer | 128/844 |
| 4,881,526 | 11/1989 | Johnson | 128/24.5 |
| 4,909,263 | 3/1990 | Norris | |

FOREIGN PATENT DOCUMENTS

| | | |
|---|---|---|
| 0178514 | 4/1986 | European Pat. Off. |
| 2387049 | 4/1978 | France |
| 2547203 | 12/1984 | France ............ 607/41 |
| 2622458 | 5/1989 | France |
| 8807819 | 9/1988 | Germany |
| 8807820 | 9/1988 | Germany |
| WO84/01515 | 4/1984 | WIPO |

OTHER PUBLICATIONS

Ivan A. Brezovich, Ph. D.; Michael B. Lilly, M.D.; John R. Durant, M.D.; and Diane B. Richards, R.N.; *A Practical System for Clinical Radiofrequency Hyperthermia*, Mar. 1981, vol. 7, pp. 423–430.

*Primary Examiner*—Michael W. Ball
*Assistant Examiner*—Michele K. Yoder
*Attorney, Agent, or Firm*—Kinney & Lange

[57] ABSTRACT

An incontinence electrode for controlling urinary incontinence in women is made of alternating bands of conductive and non-conductive polymers molded to form a tubular body. Electrical receptacles, formed in the molding process at the interior circumferential surface of the conductive polymer bands, accept metal contacts attached to electrical leads to make a secure and durable, mechanical and electrical connection between the conductive polymer bands and the leads. The leads are coupled to a controller and carry electrical current to and from the metal contacts which then distribute the current to the conductive polymer bands to cause a contraction of the vaginal muscles responsive for controlling urinary incontinence in women.

22 Claims, 5 Drawing Sheets

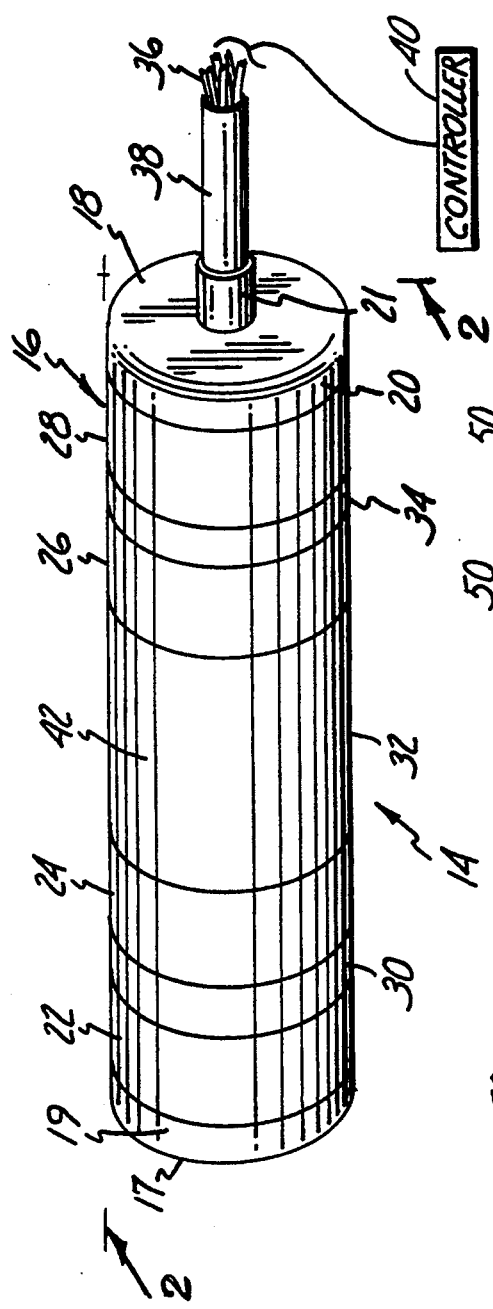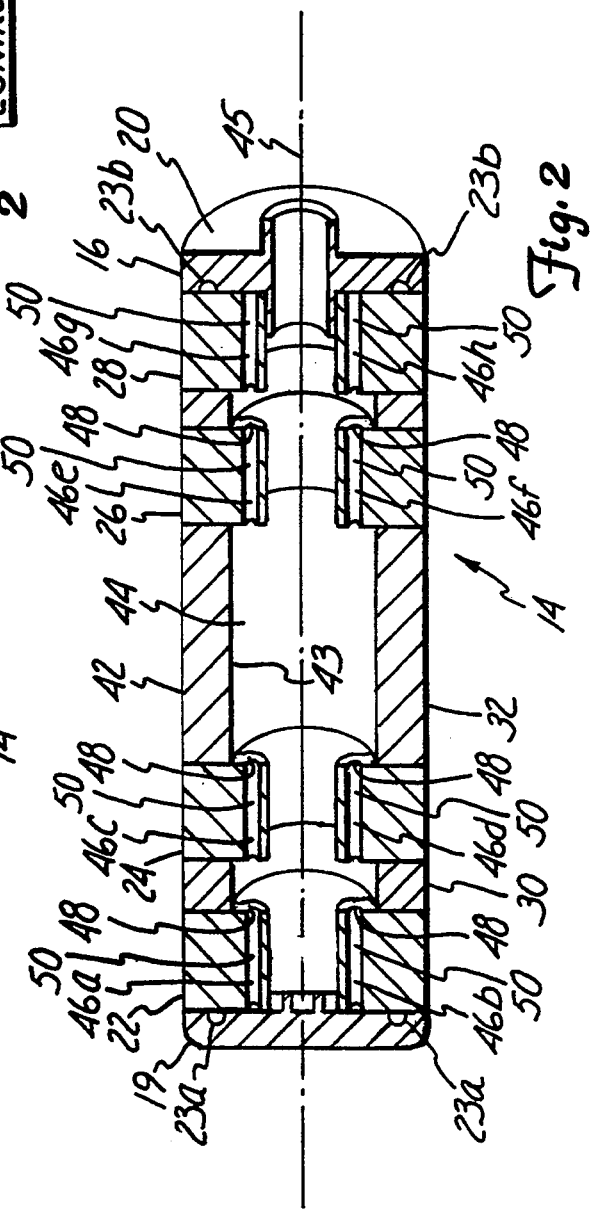

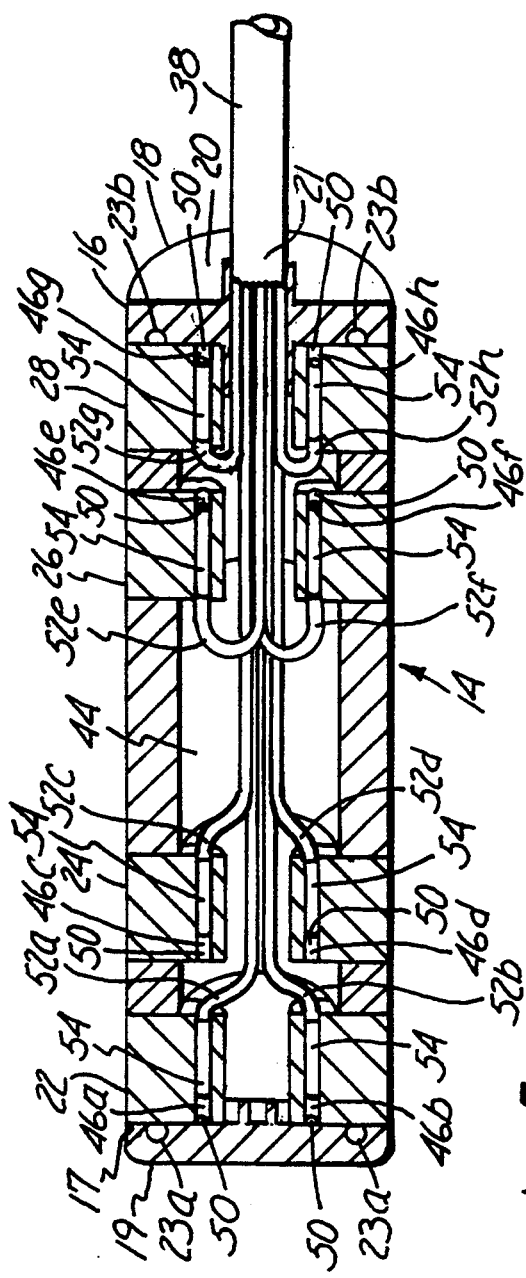
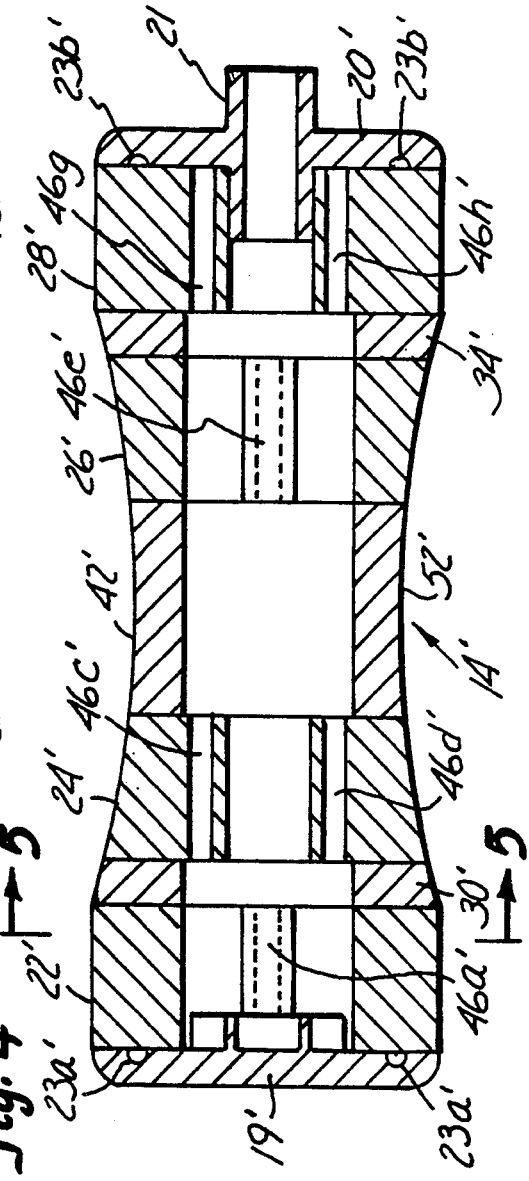
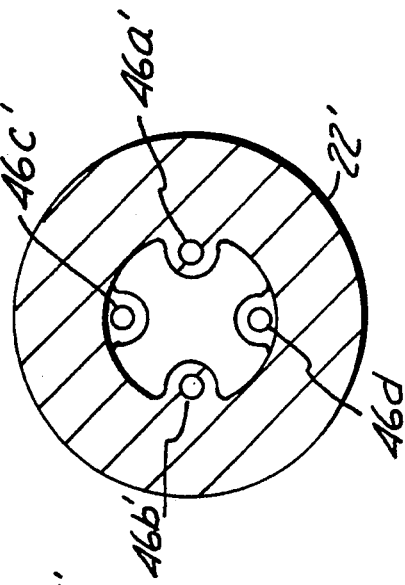

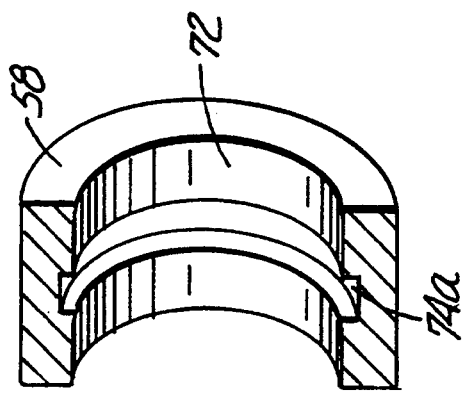
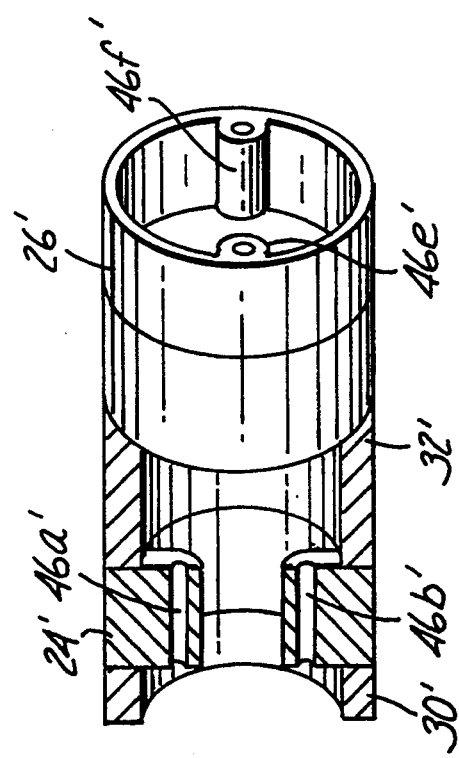
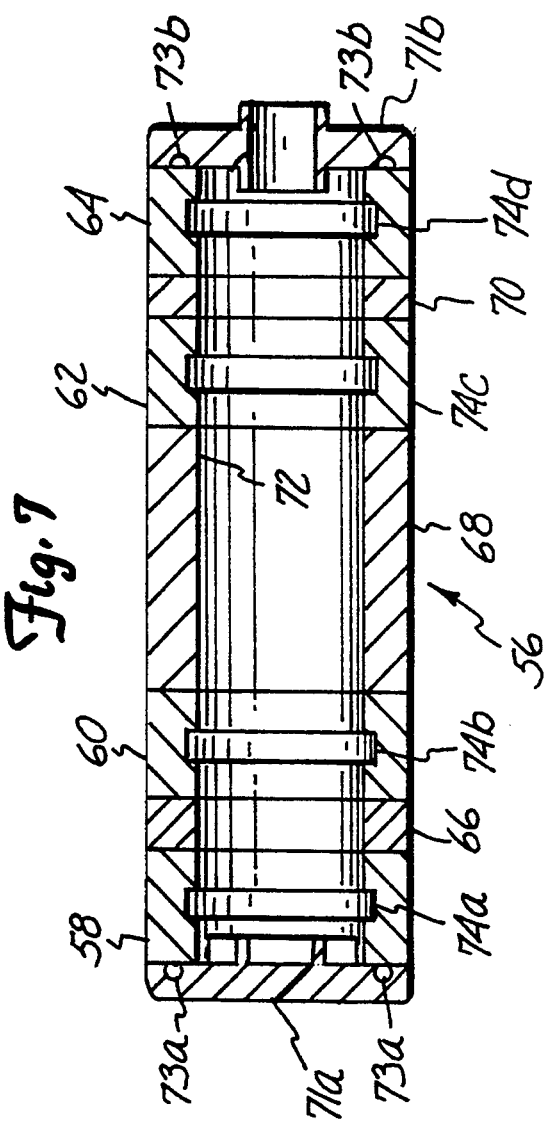

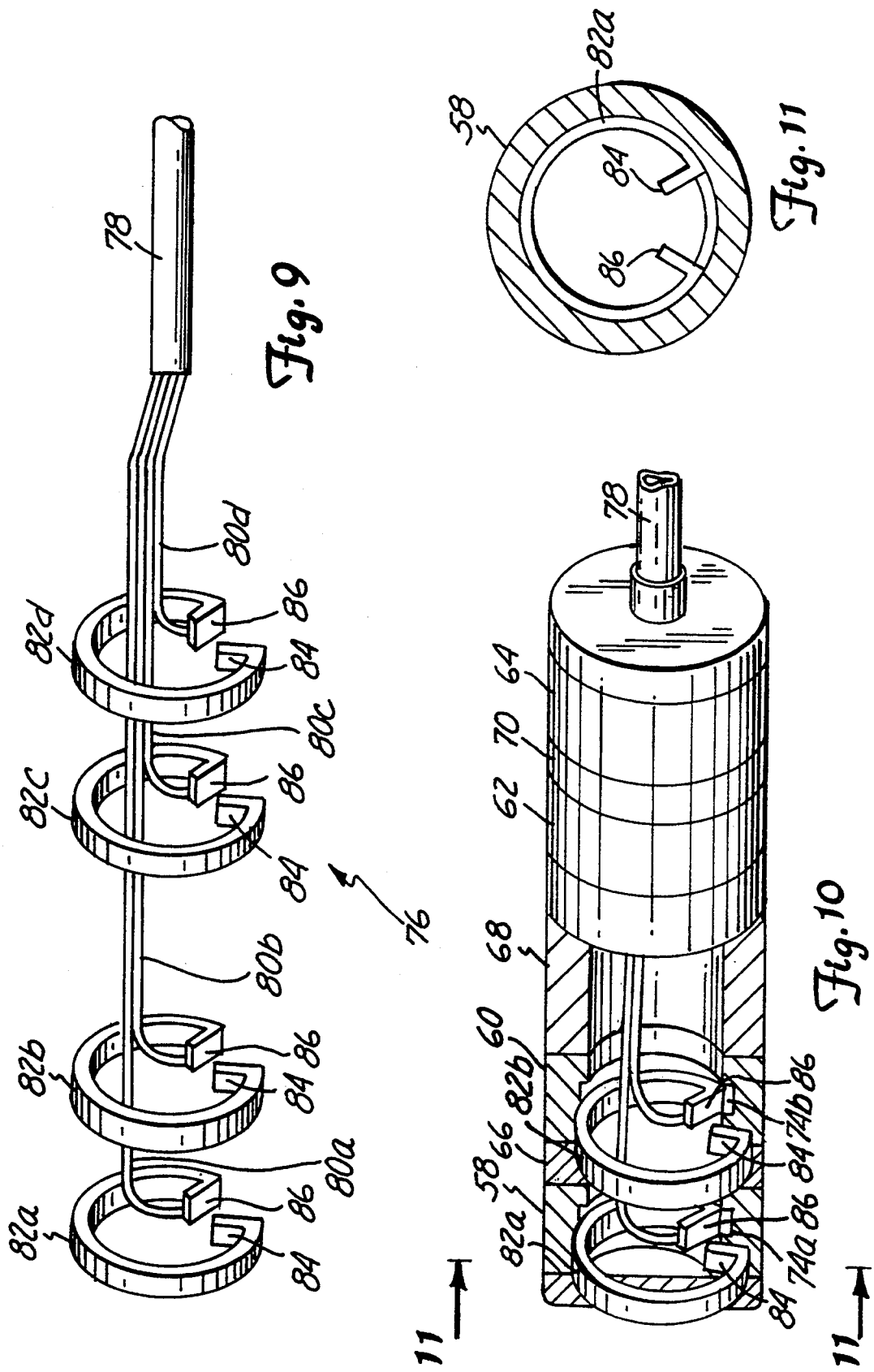

METHOD OF MAKING AN INCONTINENCE ELECTRODE

This is a divisional of application Ser. No. 07/675,568, filed Mar. 26, 1991 U.S. Pat. No. 5,199,443.

BACKGROUND OF THE INVENTION

The present invention relates generally to the field of electrical neuromuscular stimulation for controlling urinary incontinence in women. In particular, the present invention is a molded vaginal electrode having increased effectiveness and a simplified method of construction.

Electrical neuromuscular stimulation is widely used to assist persons afflicted with motor dysfunctions in performing muscle contraction maneuvers. Motor nerve fibers are electrically stimulated by means of transcutaneously applied pulses of electrical current to cause contraction of the innervated muscles. This technique is also used to re-educate patients in the proper use of the dysfunctional muscles.

For example, in cases in which urinary incontinence in women is caused by the patient's inability to properly contract the external sphincter of the urethra, it has been shown that neuromuscular stimulation of the dysfunctional muscles by means of a vaginal or anal electrode can effectively prevent the unwanted flow of urine. Furthermore, through the use of such an electrode some patients can educate themselves to voluntarily or automatically impede the flow of urine.

Electrical stimulators for controlling urinary incontinence generally include a vaginal plug with one or more electrodes in the form of conductive metal rings. The metal bands tend to cause intravaginal current density burns by the "edge effect". The "edge effect" is the tendency for the current density to be maximum at the edges of a conductor having a surface impedance considerably lower than the adjacent tissue. When the plug is inserted, the electrodes contact the vaginal wall. Conductive carbon-loaded silicon rubber substantially decreases "edge effect" to safe values, as its surface impedance can be made close to vaginal tissue impedance. Also, conductive silicone is lighter in weight than the metal electrode, which avoids the problem of the weight of the electrode causing it to fall out of the vagina. A lead harness extends from the plug to a controller or stimulator which generates stimulation signals. The controller is typically worn externally, attached to the user's clothing.

The vaginal electrode of the present invention provides an improved means for coupling electrical energy to a conductive polymer electrode. Other coupling methods such as molding the conductive polymer directly to the metal contact or using adhesives to bond the metal contact to the conductive polymer have proven ineffective. Various factors, such as heat-induced pull-away of the polymeric compounds from the metal contacts in the molding process, "stress creep" (elastomeric relaxation) of the polymeric compounds, flexing of the vaginal electrode due to contractions of the vaginal muscles, and swelling of the vaginal electrode due to absorption of vaginal fluids, have resulted in diminished contact integrity between the metal and the conductive polymer thereby increasing the electrical impedance and decreasing the effectiveness of the electrode.

There is a continuing need for improved vaginal electrodes which can be used to prevent the unwanted flow of urine. In addition to being effective, the electrode must be durable, hygienical and inexpensive to manufacture.

SUMMARY OF THE INVENTION

The present invention is a vaginal electrode adapted to be inserted into a woman's vagina for stimulating and constricting the pelvic muscles therein to prevent the flow of urine through the urethra. The vaginal electrode includes a molded, elongated tubular body composed of conductive polymer bands separated by nonconductive polymer bands. An electrical receptacle is located at the interior circumferential surface of each conductive polymer band. Leads for coupling electrical energy are attached to contacts which are then mated with the electrical receptacle to form a secure and durable mechanical connection.

In one preferred embodiment, the electrical receptacle is a cylindrical cavity within a molded domed region, which is aligned parallel to the longitudinal axis of the tubular body. The contacts include a metal pin connector, which has a diameter slightly larger than the cylindrical cavity in the molded domed region. A metal pin connector is inserted into each cavity. A reliable and durable mechanical and electrical connection to each captivated dome is created by the size differential of the metal pin connector and the cylindrical cavity of the domed region.

In another preferred embodiment, the electrical receptacle of the conductive polymer band is a circumferential groove positioned intermediate to the band width. Each contact is a metal compressible ring having an uncompressed diameter that is larger than the diameter of the grooved electrical receptacle. Each contact is compressed to reduce its diameter, inserted into the tubular body and permitted to expand when the contact is aligned with the circumferential groove. A spring-like action of the metal compressible ring and a tendency of the compressed ring to return to its uncompressed diameter make the mechanical and electrical connection to the circumferential groove reliable and durable.

The vaginal electrode of the present invention provides an improved means for coupling electrical energy to a conductive polymer electrode. Mechanical tension as a means of securing electrical leads to conductive polymers is simpler and less expensive than the bonding methods employed in the prior art. In addition, coupling electrical leads to conductive polymers by mechanical tension overcomes the problems in the prior art associated with the interrupted integrity between the electrical contact and the conductive polymers due to heat-induced pull-away of the conductive polymers from the metal contacts in the molding process, "stress creep," and flexing and swelling of the vaginal electrode during use.

This invention increases the effectiveness and useful life of the vaginal electrode. In addition, the simplified method of constructing the vaginal electrode of the present invention decreases the associated manufacturing costs.

BRIEF DESCRIPTION OF THE DRAWINGS

FIG. 1 is a perspective view of a first embodiment of a vaginal electrode in accordance with the present invention.

FIG. 2 is a sectioned perspective view taken of the vaginal electrode along line 2—2 of FIG. 1 with the electrode leads removed.

FIG. 3 is a sectioned perspective view of the vaginal electrode taken along line 2—2 of FIG. 1 with the electrode lead pin connectors positioned within electrical receptacles.

FIG. 4 is a sectional view of a second embodiment of the vaginal electrode.

FIG. 5 is a sectional view of the vaginal electrode shown in FIG. 4 taken along line 5—5.

FIG. 6 is a perspective view, with portions removed, of the vaginal electrode shown in FIG. 4.

FIG. 7 is a sectional view of a third embodiment of the vaginal electrode.

FIG. 8 is an enlarged fragmentary view of a portion of the vaginal electrode shown in FIG. 7.

FIG. 9 is a perspective view illustrating a mechanical and electrical connection assembly for the vaginal electrode shown in FIG. 7.

FIG. 10 is an cutaway perspective view the vaginal probe shown in FIGS. 7 and 8 together with the connection assembly shown in FIG. 9.

FIG. 11 is a sectional view of the vaginal electrode taken on line 11—11 of FIG. 10.

DETAILED DESCRIPTION OF THE PREFERRED EMBODIMENTS

Figure 12:
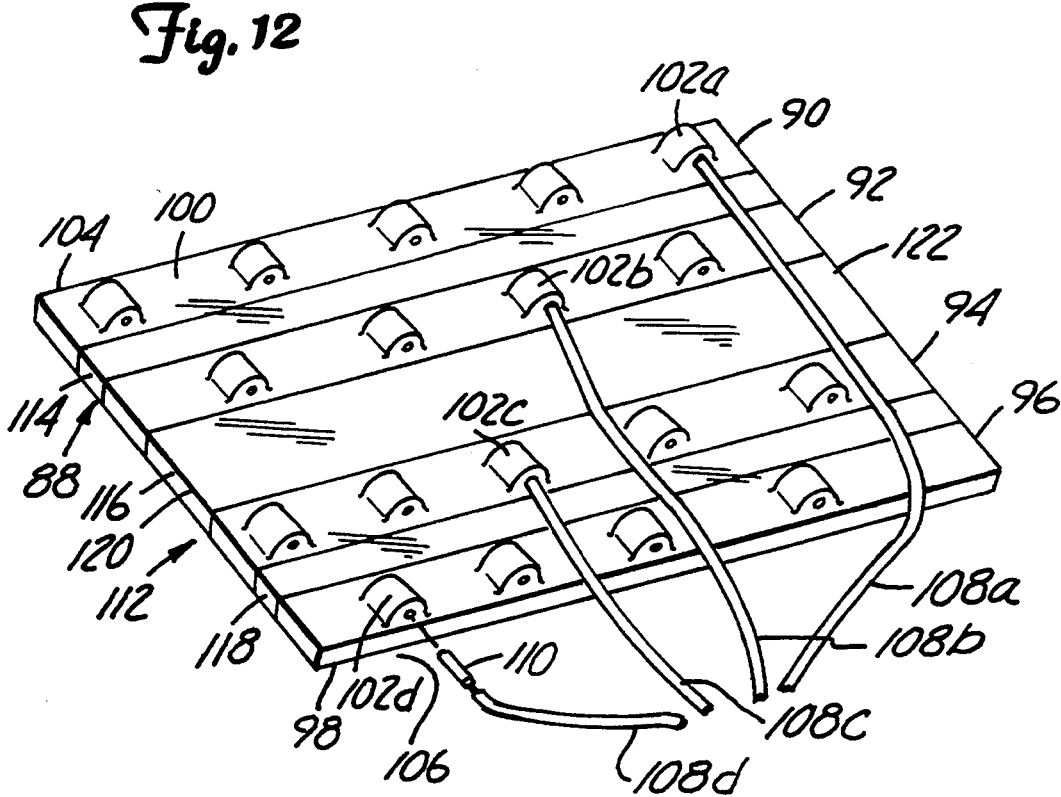
FIG. 12 is a perspective view of the fourth embodiment of the vaginal electrode in an unassembled state.

As shown in FIG. 1, a first embodiment of the present invention, vaginal electrode 14 has a cylindrically shaped tubular body 16 with a distal end 17 and a proximal end 18. The distal end 17 has a cap 19 and the proximal end 18 has a cap 20 with a sleeve 21. Vaginal electrode 14 is fabricated by a molding process, in which polymeric compounds possessing electrically conductive properties forming banded regions 22, 24, 25 and 28 are interposed with electrically non-conductive polymeric banded regions 30, 32 and 34. Initially, conductive polymers, such as carbon-loaded Silicon Rubber Rhone-Poulenc RS-1516, are injected into a mold to fabricate the individual conductive polymer bands 22, 24, 26 and 28, each having a width of about one half to about three fourths of an inch. The molded conductive polymer bands 22, 24, 26 and 28 are then positioned along a mandrel (not shown) to achieve the desired spacing of at least one sixteenth to about one half inch. The mandrel and the positioned conductive polymer bands 22, 24, 26 and 28 are then inserted into a second mold to which non-conductive polymer, such as Dow-Corning SILASTIC® Q7-4535, is injected to connect the conductive polymer bands 22, 24, 26 and 28 and thereby form tubular body 16 of vaginal electrode 14. The tubular body 16 is then cured to effect the chemical bonding of conductive polymer bands 22, 24, 26 and 28 to non-conductive polymer bands 30, 32 and 34.

Electrical leads 36, which are housed in lead harness 38, are coupled to controller 40 and carry electrical current to conductive bands 22, 24, 26 and 28. Conductive bands 22, 24, 26 and 28 are positioned along tubular body 16 to carry electrical current to and from the appropriate regions of the vaginal wall (not shown) while inserted in the vagina, thereby effecting contraction of the muscles which obstruct the urinary flow. The molded cylindrical body 16 has a smooth, streamlined, hygienical exterior surface 42, which makes vaginal electrode 14 easily maintainable and reusable. The circumference of exterior surface 42 ranges from about 2.42 to about 3.20 inches.

FIG. 2 is a sectional perspective view taken of the vaginal electrode 14 along line 2—2 of FIG. 1. Vaginal electrode 14 has an interior circumferential surface 43, cavity 44 and longitudinal axis 45, with receptacles 46a–46h at conductive polymer bands 22, 24, 26 and 28. The distance from exterior surface 42 to interior circumferential surface 43 is about 0.14 to about 0.26 inches. Receptacles 46a–46h, which are formed in the molding process, include domed regions 48 and cylindrical cavities 50. Each cavity 50 has a diameter of about 0.070 inches and a longitudinal axis parallel to the longitudinal axis 45 of the tubular body 16. In the first embodiment, receptacles 46a, 46c, 46e and 46g, and receptacles 46b, 46d, 46f and 46h are coaxially aligned, respectively. Receptacles 46a, 46c, 46e and 46g are positioned 180 degrees from receptacles 46b, 46d, 46f and 46h, respectively.

FIG. 3 is also a sectional perspective view of the vaginal electrode taken along line 2—2 of FIG. 1, but with the electrical leads in place. Lead harness 36 extends into vaginal electrode 14 through sleeve 21 of proximal end cap 20 and delivers leads 52a–52h into the cavity 44 of vaginal electrode 14. Leads 52a–52h terminate in a pin-type connector 54a–54h, respectively. Each pin connector 54a–54h is formed of metal, such as gold-coated brass, and has a diameter about 0.01 inches larger than cavity 50 of receptacles 46a–46h. Pin connectors 54a–54h are attached to leads 52a–52h by any acceptable manner, such as crimping and/or soldering. Pin connectors 54a–54d are then inserted in a first direction in receptacles 46a–46d, respectfully. Pin connectors 54e–54h are inserted in a second direction, opposite the first direction, into receptacles 46e–46h, respectfully. Because the diameter of each pin connector 54a–54h is slightly larger than the diameter of cavity 50 of receptacles 46a–46h, electrical connection of leads 52a–52h is accomplished by a durable and reliable mechanical tension. Thus, despite "stress creep" (elastomeric relaxation) of the polymeric compounds of vaginal electrode 14, flexing of vaginal electrode 14 due to the contractive forces of the vaginal muscles, or swelling of the polymeric compounds of vaginal electrode 14 due to the absorption of vaginal membrane fluids, the connection of pin connectors 54a–54h to receptacles 46a–46h, respectfully, provides a continuous mechanical and electrical contact.

A premolded distal end cap 19, interposed by an O-ring gasket 23a for an improved seal, is adhered to the distal end 17 of tubular body 16 by a medical grade adhesive, such as Dow-Corning SILASTIC® Medical Adhesive Type A. Likewise, a premolded proximal end cap 20, interposed by O-ring gasket 23b for an improved seal, is adhered to the proximal end 18 of tubular body 16. Lead harness 38 is also adhered to sleeve 21 of proximal end cap 20 by a medical grade adhesive, thereby completing the construction process of vaginal electrode 14.

FIGS. 4–6 illustrate a second preferred embodiment of the present invention, which is constructed in a manner similar to the first preferred embodiment. FIG. 4 is a sectional view vaginal electrode 14'. Vaginal electrode 14' has conductive polymer bands 22', 24', 26', and 28', which are interposed by non-conductive polymer bands 30', 32' and 34', in a manner similar to the first embodiment shown in FIGS. 1 and 2. The second preferred embodiment, however, differs from the first embodiment in two ways. First, exterior surface 42' is gradually and slightly tapered between conductive polymer bands 22' and 28'. The tapered exterior surface 42' facilitates the positioning and retention of vaginal electrode 14' within the vagina. Electrical current delivered to the conductive polymer bands 22', 24', 26' and 28' causes the dysfunctional pelvic muscles to contract. This muscle contraction causes the vaginal wall to bear down on the vaginal electrode 14' in a non-uniform manner so as to conform to the tapered shape of the exterior surface 42', thereby maintaining vaginal electrode 14' in the desired location.

Second, conductive polymer bands 22' and 26' are axially rotated 90 degrees in the second embodiment, thereby relocating receptacles 46a'–46b' and 46e'–46f' (46b' and 46f' are not shown). As shown in FIGS. 5 and 6, the axial rotation of conductive polymer bands 22+ and 26' axially positions receptacles 46a'–46b' and 46e'–46f' 90 degrees to receptacles 46c'–46d' and 46g' and 46h'. This positioning facilitates the mechanical and electrical connection of the leads by improving access to receptacles 46a'–46b' and 46e'–46f'. (For ease of illustration, the electric leads are not shown in FIGS. 4–6, but are similar to leads 52a–52h of FIG. 3).

FIGS. 7–11 illustrate a third embodiment of the present invention, which is constructed in a manner similar to the first preferred embodiment. FIG. 7 is a sectional view of vaginal electrode 56. Vaginal electrode 56 is configured similar to the first and second embodiments with conductive polymer bands 58, 60, 62 and 64 interposed by non-conductive polymer bands 66, 68 and 70, and with distal end cap 71a and proximal end cap 71b. In the third embodiment, however, interior circumferential surface 72 of conductive polymer bands 58, 60, 62, and 64 have grooves 74a–74d, respectfully, positioned intermediate to the width of conductive polymer bands 58, 60, 62, and 64. FIG. 8 is an enlarged perspective view of the interior circumferential groove 74a to demonstrate that grooves 74a–74d create a channel, which subsequently serves as an electrical receptacle.

FIG. 9 is a perspective view of an electrical connection assembly 76 for the third embodiment for use with vaginal electrode 56 shown in FIG. 7. Electrical connection assembly 76 includes a lead harness 78, which houses electrical leads 80a–80d. Leads 80a–80 d are connected to ring contacts 82a–82d, respectfully. Ring contacts 82a–82d are formed of a resilient metal, such as gold-coated brass. Each ring contact 82a–82d is discontinuous and has terminal ends that are bent inwardly to form tabs 84 and 86. Tables 84 and 86 facilitate compression of ring contacts 82a–82d. Even ring contact 82a–82d has a width which is slightly smaller than that of grooves 74a–74d of FIG. 7. In addition, the uncompressed external diameter of each ring contact 82a–82d shown in FIG. 9 is larger than the diameter of grooves 74a–74d shown in FIG. 7.

FIG. 10 is a cutaway perspective view of the vaginal electrode shown in FIG. 7 together with the electrical connection assembly shown in FIG. 9. Each ring contact 82a–82d (ring contact 82c and 82d not shown) is installed by: compressing each ring contact 82a–82d by a force exerted on tabs 84 and 86; inserting each compressed ring 82a–82d into the cavity of vaginal electrode 56; aligning each compressed ring 82a–82d with each groove 74a–74d, respectively (grooves 74c and 74d not shown); and releasing tables 84 and 86, thereby permitting each ring contact 82a–82d to expand and make a durable and reliable mechanical and electrical connection to grooves 74a–74d, respectively, as shown in FIG. 11. Ring contacts 82a–82d, by virtue of their circumferential contact with grooves 74a–74d, respectfully, provide a uniform distribution of current throughout the exterior surface of conductive polymer bands 58-64. Additionally, the method of electrical connection just described, similar to the advantages described in the first embodiment, provides a continuous mechanical and electrical contact to the conductive polymer rings despite "stress creep" (elastomeric relaxation) of the polymers, flexing of vaginal electrode 56 due to the contractive forces of the vaginal muscles, and swelling of the polymers due to absorption of vaginal membrane fluids while inserted in the vaginal cavity. The mechanical and electrical connection just described is accomplished through a spring action, as shown in FIG. 11; the compressed ring contacts 82a–82d continually attempt to expand to their uncompressed diameter.

FIG. 12 is a perspective view of the fourth embodiment of the vaginal electrode 88 in an unassembled state, for purposes of illustrating a second method of construction. Conductive polymers are injected into a mold to fabricate the individual conductive polymer bands 90, 92, 94 and 96, each having a width of about one half to about three fourths of an inch, and a first major surface 98 and a second major surface 100. At least one electrical receptacle 102a–102d is formed in the molding process at the second major surface 100 of each conductive polymer band 90, 92, 94 and 96, respectively. The molded conductive polymer bands 90, 92, 94 and 96 are then positioned on a mandrel (not shown) to achieve the desired spacing of at least one sixteenth to about one half inch. Conductive polymer band 90 is positioned at a distal end and conductive polymer band 96 is positioned at a proximal end. Electrical leads 108a–108d, each terminating in a pin-type contact 110, are inserted into receptacles 102a–102d, respectively, in a proximal-to-distal direction to make mechanical and electrical connection. The mandrel and the positioned conductive polymer bands 90, 92, 94 and 96 are then inserted into a mold to which non-conductive polymer is added in between conductive polymer bands 90, 92, 94 and 96 to connect conductive polymer bands 90, 92, 94 and 96 and to cover the second surface 98, including receptacles 102a–102d and leads 108a–108d, thereby forming an integral electrode body 112 having non-conductive bands 114, 116 and 118. The integral electrode body also has a left edge 120 and a right edge 122.

Figure 13:
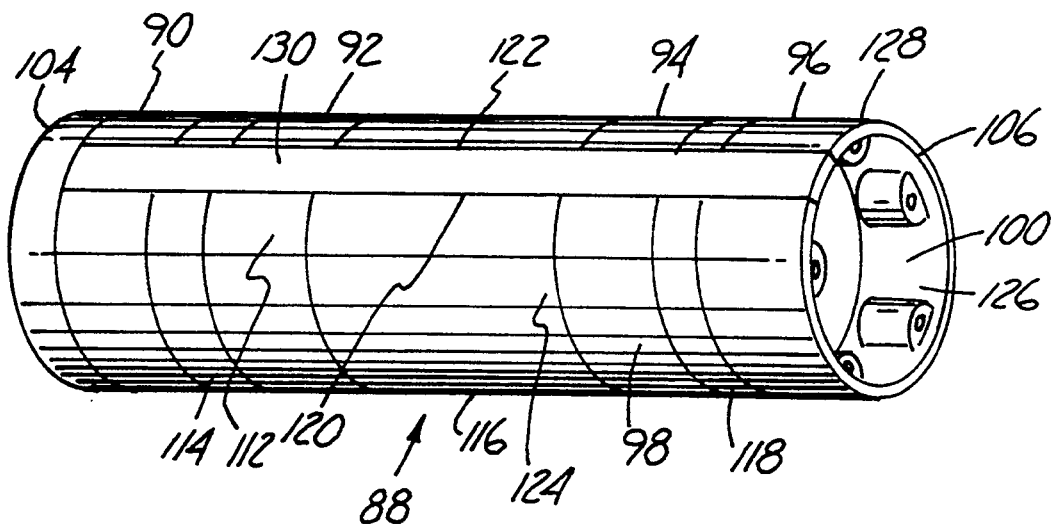
FIG. 13 is a perspective view of the vaginal electrode shown in FIG. 12 in a rolled-up state.

FIG. 13 is a perspective view of the vaginal electrode 88 shown in FIG. 12 in a rolled-up state (electrical leads 108a–108d of FIG. 12 not shown). Left edge 120 is rolled toward right edge 122, thereby placing left edge 120 and right edge 122 in close proximity and generally configuring the integral electrode body 112 into a tubular form, with the first major surface 98 forming the exterior circumferential surface 124 and the second major surface 100 forming the interior circumferential surface 126 of vaginal electrode 88. The rolled integral electrode body 112, supported by a mandrel (not shown), is then placed into another mold, to which non-conductive polymer is added in between the left edge 120 and right edge 122 to connect left edge 120 with right edge 122, thereby forming a contiguous exterior surface 124 and interior surface 126 of tubular integral electrode body 128. The non-conductive polymer that bonds the left edge 120 and the right edge 122 forms a narrow non-conductive polymer strip 130 that extends from the distal end 104 to the proximal end 106 of the tubular integral electrode body 128. The narrow non-conductive polymer strip 130, while making conductive polymer bands 90, 92, 94 and 96 dis-contiguous, is so negligible in dimension as to not interfere in the functioning of vaginal electrode 88. Construction of vaginal electrode 88 is completed by bonding caps 104 and 106 to the distal and proximal ends, respectively, of vaginal electrode 88 in a manner similar to the previous embodiments (proximal end cap 106 and O-ring gaskets now shown). Finally, the lead harness (not shown) is adhered to the sleeve (not shown) of the proximal end cap to conclude the construction of vaginal electrode 88.

The various embodiments of the invention described herein are more reliable, inexpensive and easier to manufacture than similar inventions described in the prior art. The result is a vaginal electrode that is more effective, has a longer useful life and is reusable, hygienical and reliable during extensive use.

Although the present invention has been described with reference to preferred embodiments, workers skilled in the art will recognize that changes may be made in form and detail without departing from the spirit and scope of the invention.

What is claimed is:

1. A method for making an electrode, the method comprising:
   molding bands of conductive polymer such that each band of conductive polymer includes an interior circumferential surface;
   positioning an electrical receptacle at the interior circumferential surface of each band of conductive polymer, wherein each electrical receptacle includes a doomed region with a cylindrical cavity;
   molding non-conductive polymer between the conductive polymer bands to form a tubular body with a distal and a proximal end; and
   inserting contacts coupled to electrical leads into the tubular body from the proximal end, wherein each contact has an outer diameter which is greater than an inner diameter of each corresponding electrical receptacle such that the contacts make a mechanical and electrical connection with the receptacles.

2. The method of claim 1 and further comprising:
   adhering a non-conductive polymer cap to the distal end of the body; and
   adhering a non-conductive polymer cap having a sleeved access for the leads to the proximal end of the body.

3. The method of claim 2 wherein the leads are housed in a lead harness.

4. The method of claim 3 and further comprising:
   adhering the lead harness to the sleeved access.

5. The method of claim 1 wherein spacing of the conductive polymer bands is performed by placing the conductive polymer bands on a mandrel.

6. A method of making an electrode, the method comprising:
   forming conductive polymer bands such that each band includes first and second major surfaces;
   positioning a first electrical receptacle on a second major surface of a first conductive polymer, wherein the first electrical receptacle includes a doomed region with a cylindrical cavity;
   positioning a second electrical receptacle on a second major surface of a second conductive polymer, wherein the second electrical receptacle includes a doomed region with a cylindrical cavity;
   connecting a first electrical contact the first electrical receptacle, wherein the first electrical contact has an outer diameter which is greater than an inner diameter of the first receptacle;
   connecting a first electrical contact to the second electrical receptacle, wherein the second electrical contact has an outer diameter which is greater than an inner diameter of the second receptacle;
   supporting the bands of conductive polymer in spaced relationship; and
   forming non-conductive polymer bands between the conductive polymer bands to produce an integral electrode body having alternating conductive and non-conductive polymer bands.

7. The method of claim 6 and further comprising:
   inserting first and second contacts into the first and second electrical receptacles to make a mechanical and electrical connection.

8. The method of claim 6 wherein spacing of the conductive polymer bands is performed by placing the conductive polymer bands on a mandrel, and wherein non-conductive polymer is molded between the conductive polymer bands and over the second major surface to form the integral electrode body.

9. The method of claim 8 wherein the conductive polymer bands are generally tubular, with the first major surface facing outward and the second major surface facing inward, and wherein the integral electrode body is a tubular body having a proximal end and a distal end.

10. The method of claim 9 and further comprising:
    inserting first and second electrical leads connected to the first and second contacts into the integral electrode body from the proximal end, such that the first and second contacts make a mechanical and electrical connection with the first and second electrical receptacles.

11. The method of claim 10 and further comprising:
    adhering a non-conductive polymer cap to the distal end of the body; and
    adhering a non-conductive polymer cap having a sleeved access for the first and second electrical leads to the proximal end of the body.

12. The method of claim 11 wherein the first and second electrical leads are housed in a lead harness.

13. The method of claim 12 and further comprising:
    adhering the lead harness to the sleeved access.

14. A method of making an electrode, the method comprising;
    molding a plurality of conductive polymer bands such that each conductive polymer band has a width and an electrical receptacle at an inner surface, wherein the electrical receptacle includes a doomed region with a cylindrical cavity having an inner diameter;
    supporting the plurality of conductive polymer bands in a spaced relationship;
    forming at least one non-conductive polymer band between the plurality of conductive polymer bands to produce an integral electrode body having alternating conductive and non-conductive polymer bands; and
    mating a plurality of electrical contacts to the plurality of electrical receptacles, wherein each electrical contact of the plurality of electrical contacts has an outer diameter which is greater than the inner diameter of each, corresponding electrical receptacle of the plurality of a electrical receptacles so as to make a mechanical and electrical connection between the plurality of conductive polymer bands and the plurality of contacts.

15. A method of claim 14 wherein each electrical contact of the plurality of electrical contacts is a metal pin.

16. The method of claim 15 wherein the cylindrical cavity has a longitudinal axis generally parallel to a longitudinal axis of the tubular body.

17. The method of claim 14 wherein the conductive polymer bands have widths along the longitudinal axis of about one-half to about three-fourths inch.

18. The method of claim 17 wherein the conductive polymer bands have a separation of about one-sixteenth to about one-half inch.

19. The method of claim 14 and further comprising:
molding a distal endcap located at a distal end of the elongated tubular body.

20. The method of claim 19 and further comprising;
molding a proximal endcap to a proximal end of the elongated tubular body.

21. The method of claim 6 wherein the conductive and non-conductive polymer bands are flat bands, the method further comprising:
rolling the integral electrode body into a tubular form; and
bonding adjacent edges of the body to form a tubular integral electrode body.

22. The method of claim 21 wherein non-conductive polymer is molded between adjacent edges of the body to form the tubular integral electrode body.

* * * * *

UNITED STATES PATENT AND TRADEMARK OFFICE
CERTIFICATE OF CORRECTION

PATENT NO. : 5,376,206
DATED : December 27, 1994
INVENTOR(S) : DONALD D. MAURER, ALEXANDER KIPNIS It is certified that error appears in the above-indentified patent and that said Letters Patent is hereby corrected as shown below:

On the Title Page of the Patent, line 13 of [57] ABSTRACT, delete "responsive", insert --responsible--

Col. 3, line 43, delete "carbon-loaded", insert --Carbon-loaded--

Col. 4, line 5, delete "sectional", insert --sectioned--

Col. 5, line 17, delete "46f", insert --46f'--

Col. 5, line 18, delete "46f", insert --46f'--

Col. 5, line 19, delete "22+", insert --22'--

Col. 5, line 40, delete "74ato", insert --74a to--

Col. 5, line 47, delete "80 d", insert --80d--

Col. 7, line 36, delete "doomed", insert --domed--

Col. 7, line 66, delete "doomed", insert --domed--

Col. 8, line 2, delete "doomed", insert --domed--

Signed and Sealed this

Twenty-first Day of March, 1995

Attest:

BRUCE LEHMAN

*Attesting Officer*      *Commissioner of Patents and Trademarks*